United States Patent
White et al.

(10) Patent No.: US 9,919,151 B2
(45) Date of Patent: *Mar. 20, 2018

(54) CURRENT CONTROL FOR ELECTROTRANSPORT DRUG DELIVERY

(71) Applicants: Incline Therapeutics, Inc., Redwood City, CA (US); Alza Corporation, Vacaville, CA (US)

(72) Inventors: Bradley E. White, Lebanon, OH (US); Paul Hayter, Mountain View, CA (US); John Lemke, Pleasanton, CA (US); Scot Satre, Brentwood, CA (US); Corinna X. Chen, Oakland, CA (US); Brian W. Read, Brier, WA (US); Jason E. Dougherty, Seattle, WA (US)

(73) Assignees: Incline Therapeutics, Inc., Redwood City, CA (US); Alza Corporation, Vacaville, CA (US)

( * ) Notice: Subject to any disclaimer, the term of this patent is extended or adjusted under 35 U.S.C. 154(b) by 399 days.

This patent is subject to a terminal disclaimer.

(21) Appl. No.: 14/406,969

(22) PCT Filed: Mar. 5, 2013

(86) PCT No.: PCT/US2013/029114
§ 371 (c)(1),
(2) Date: Dec. 10, 2014

(87) PCT Pub. No.: WO2013/187951
PCT Pub. Date: Dec. 19, 2013

(65) Prior Publication Data
US 2015/0196754 A1    Jul. 16, 2015

Related U.S. Application Data

(63) Continuation of application No. 13/493,314, filed on Jun. 11, 2012, now Pat. No. 8,428,709.

(51) Int. Cl.
*A61N 1/32* (2006.01)
*A61N 1/30* (2006.01)
*A61N 1/02* (2006.01)

(52) U.S. Cl.
CPC .............. *A61N 1/325* (2013.01); *A61N 1/025* (2013.01); *A61N 1/30* (2013.01)

(58) Field of Classification Search
CPC .......... A61N 1/325; A61N 1/025; A61N 1/30; G05F 1/40; G05F 1/56; H02M 3/155–3/157
(Continued)

(56) References Cited

U.S. PATENT DOCUMENTS 3,521,641 A * 7/1970 Farensbach ........ A61N 1/36014
331/113 A
4,141,359 A   2/1979 Jacobsen et al.
(Continued)

FOREIGN PATENT DOCUMENTS

CN    1099300 C    1/2003
CN    1972681 A    5/2007
(Continued)

OTHER PUBLICATIONS

White et al.; U.S. Appl. No. 13/866,371 entitled "Self-test for analgesic product," filed Apr. 19, 2013.
(Continued)

*Primary Examiner* — Bhisma Mehta
*Assistant Examiner* — Larry R Wilson
(74) *Attorney, Agent, or Firm* — Shay Glenn LLP (57) ABSTRACT

Devices, systems and methods for controlling the application of current and/or voltage to deliver drug from patient contacts of an electrotransport drug delivery device by indirectly controlling and/or monitoring the applied current without directly measuring from the cathode of the patient
(Continued)

terminal. In particular, described herein are electrotransport drug delivery systems including constant current delivery systems having a feedback current and/or voltage control module that is isolated from the patient contacts (e.g., anodes and cathodes). The feedback module may be isolated by a transistor from the patient contacts; feedback current and/or voltage control measurements may be performed at the transistor rather than at the patient contact (e.g., cathode).

20 Claims, 5 Drawing Sheets

(58) Field of Classification Search
USPC ............. 604/20, 21, 500, 501; 607/62–64; 323/265, 282–290
See application file for complete search history.

(56) References Cited

U.S. PATENT DOCUMENTS

| | | |
|---|---|---|
| 4,474,570 A | 10/1984 | Ariura et al. |
| 4,588,580 A | 5/1986 | Gale et al. |
| 4,698,582 A | 10/1987 | Braun et al. |
| 4,731,926 A | 3/1988 | Sibalis |
| 4,752,285 A | 6/1988 | Petelenz et al. |
| 4,822,802 A | 4/1989 | Levy et al. |
| 4,878,892 A | 11/1989 | Sibalis et al. |
| 4,931,046 A | 6/1990 | Newman |
| 5,006,108 A | 4/1991 | LaPrade |
| 5,019,034 A | 5/1991 | Weaver et al. |
| 5,047,007 A | 9/1991 | McNichols et al. |
| 5,057,072 A | 10/1991 | Phipps |
| 5,084,008 A | 1/1992 | Phipps |
| 5,135,477 A | 8/1992 | Untereker et al. |
| 5,135,479 A | 8/1992 | Sibalis et al. |
| 5,147,297 A | 9/1992 | Myers et al. |
| 5,199,155 A | 4/1993 | Cord et al. |
| 5,203,768 A | 4/1993 | Haak et al. |
| 5,224,927 A | 7/1993 | Tapper |
| 5,224,928 A | 7/1993 | Sibalis et al. |
| 5,232,438 A | 8/1993 | Theeuwes et al. |
| 5,232,448 A | 8/1993 | Zdeb |
| 5,246,418 A | 9/1993 | Haynes et al. |
| 5,254,081 A | 10/1993 | Maurer et al. |
| 5,306,235 A | 4/1994 | Haynes |
| 5,314,502 A | 5/1994 | McNichols et al. |
| H1324 H | 6/1994 | Dalke et al. |
| 5,320,597 A | 6/1994 | Sage, Jr. et al. |
| 5,358,483 A | 10/1994 | Sibalis |
| D352,357 S | 11/1994 | Ashley |
| 5,445,609 A | 8/1995 | Lattin et al. |
| 5,458,569 A | 10/1995 | Kirk, III et al. |
| D372,098 S | 7/1996 | Lattin et al. |
| 5,551,953 A | 9/1996 | Lattin et al. |
| 5,562,607 A | 10/1996 | Gyory |
| 5,603,693 A | 2/1997 | Frenkel et al. |
| 5,644,463 A | 7/1997 | El-Sharkawi et al. |
| D384,745 S | 10/1997 | Lattin et al. |
| 5,688,232 A | 11/1997 | Flower |
| 5,697,896 A | 12/1997 | McNichols et al. |
| 5,718,562 A | 2/1998 | Lawless et al. |
| 5,804,957 A * | 9/1998 | Coln ............. A61N 1/0432 323/282 |
| 5,843,014 A | 12/1998 | Lattin et al. |
| 5,879,143 A | 3/1999 | Cote et al. |
| 5,919,155 A | 7/1999 | Lattin et al. |
| 5,928,196 A | 7/1999 | Johnson et al. |
| 5,983,133 A * | 11/1999 | Garde ............. A61N 1/30 604/20 |
| 6,029,083 A | 2/2000 | Flower et al. |
| 6,035,234 A | 3/2000 | Riddle et al. |
| 6,039,977 A | 3/2000 | Venkatraman et al. |
| 6,047,208 A | 4/2000 | Flower |
| 6,049,733 A | 4/2000 | Phipps et al. |
| 6,086,572 A | 7/2000 | Johnson et al. |
| 6,167,302 A | 12/2000 | Millot |
| 6,171,294 B1 | 1/2001 | Southam et al. |
| 6,181,963 B1 | 1/2001 | Chin et al. |
| 6,216,033 B1 | 4/2001 | Southam et al. |
| 6,295,469 B1 | 9/2001 | Linkwitz et al. |
| 6,355,025 B1 | 3/2002 | Phipps et al. |
| 6,385,488 B1 | 5/2002 | Flower et al. |
| 6,425,892 B2 | 7/2002 | Southam et al. |
| 6,453,195 B1 | 9/2002 | Thompson |
| 6,881,208 B1 | 4/2005 | Phipps et al. |
| 6,949,081 B1 | 9/2005 | Chance |
| 6,970,739 B1 | 11/2005 | Inoue |
| 6,975,902 B2 | 12/2005 | Phipps et al. |
| 7,016,724 B2 | 3/2006 | Henley et al. |
| 7,027,859 B1 | 4/2006 | McNichols et al. |
| 7,302,293 B2 | 11/2007 | Southam et al. |
| 7,597,679 B2 | 10/2009 | Jespersen et al. |
| 7,621,893 B2 | 11/2009 | Moberg et al. |
| 7,660,627 B2 | 2/2010 | McNichols et al. |
| 7,766,873 B2 | 8/2010 | Moberg et al. |
| 7,844,326 B2 | 11/2010 | Dent et al. |
| 8,301,238 B2 | 10/2012 | Netzel et al. |
| 8,428,708 B1 | 4/2013 | White et al. |
| 8,428,709 B1 | 4/2013 | White et al. |
| 2002/0128591 A1 | 9/2002 | Kleiner et al. |
| 2002/0165481 A1 | 11/2002 | Hoffmann et al. |
| 2002/0183702 A1 | 12/2002 | Henley et al. |
| 2002/0198504 A1 | 12/2002 | Risk et al. |
| 2003/0191946 A1 | 10/2003 | Auer et al. |
| 2004/0085215 A1 | 5/2004 | Moberg et al. |
| 2005/0004506 A1 | 1/2005 | Gyory |
| 2006/0025715 A1 | 2/2006 | Henley et al. |
| 2006/0161827 A1 | 7/2006 | Gohel et al. |
| 2007/0035903 A1 | 2/2007 | Sullivan et al. |
| 2008/0234627 A1 | 9/2008 | Dent et al. |
| 2008/0234628 A1 | 9/2008 | Dent et al. |
| 2009/0043244 A1 | 2/2009 | Inan |
| 2009/0171502 A1 | 7/2009 | Freidin |
| 2010/0037680 A1 | 2/2010 | Moberg et al. |
| 2012/0253262 A1 | 10/2012 | Lemke et al. |
| 2015/0338445 A1 | 11/2015 | White et al. |

FOREIGN PATENT DOCUMENTS

| | | |
|---|---|---|
| CN | 102421480 | 4/2012 |
| EP | 1084729 A2 | 3/2001 |
| EP | 1532995 | 5/2005 |
| GB | 2239803 A | 7/1991 |
| JP | H04-208166 A | 7/1992 |
| JP | H05-004482 U | 1/1993 |
| JP | 05508558 A | 12/1993 |
| JP | H06-62433 U | 9/1994 |
| JP | 07-067971 | 3/1995 |
| JP | 07-124265 | 5/1995 |
| JP | 11-128369 A | 5/1999 |
| JP | H11-505445 A | 5/1999 |
| JP | 2000157320 A | 6/2000 |
| JP | 2001120669 A | 5/2001 |
| JP | 2003260144 A | 9/2003 |
| JP | 200939553 A | 2/2009 |
| KR | 97000259 B1 | 3/1997 |
| NZ | 541949 A | 11/2008 |
| RU | 2232608 C2 | 7/2004 |
| RU | 2269368 C1 | 2/2006 |
| WO | WO 90/03825 A1 | 4/1990 |
| WO | WO 91/15257 A1 | 10/1991 |
| WO | WO 91/15258 A1 | 10/1991 |
| WO | WO 93/01807 A1 | 2/1993 |
| WO | WO 95/27530 A1 | 10/1995 |
| WO | WO 96/36394 A1 | 11/1996 |
| WO | WO 97/07854 A1 | 3/1997 |
| WO | WO 99/30773 A1 | 6/1999 |
| WO | WO 01/41863 A1 | 6/2001 |
| WO | WO 2006/077262 A1 | 7/2006 |
| WO | WO 2009/120840 A2 | 10/2009 |
| WO | WO 2010/078313 A1 | 7/2010 |

(56) References Cited

FOREIGN PATENT DOCUMENTS

OTHER PUBLICATIONS

Ahmad et al.; Fentanyl HCI iontophoretic transdermal system versus intravenous morphine pump after gynecologic surgery; Arch Gynecol Obstet; vol. 276, No. 3; pp. 251-258; Sep 2007.
Chelly, Jacques E.; An intophoretic, fentanyl HCI patient-controlled transdermal system for acute postoperative pain management; Expert Opin. Pharmacother.; vol. 6; No. 7; pp. 1205-1214; Jun 2005.
Grond et al.; Iontophoretic transdermal system using fentanyl compared with patient-controlled intravenous analgesia using morphine for postoperative pain management; British Journal of Anaesthesia; vol. 98; No. 6; pp. 806-815; Jun. 2007.
Minkowitz et al.; Safety and tolerability of fentanyl iontophoretic transdermal system: Findings from a pooled data analysis of four clinical trials; Journal of Opioid Management; vol. 6; No. 3; pp. 203-210; May/Jun. 2010.
Sathyan et al.; Passive absorption of fentanyl from the fentanyl HCI iontophoretic transdermal system; Current Medical Research and Opinion; vol. 25; No. 2; pp. 363-366; Feb. 2009.
Viscusi, Eugene; Patient-controlled drug delivery for acute postoperative pain management: A review of current and emerging technologies; Regional Anesthesia and Paid Medicine; vol. 33; No. 2; pp. 146-158; Mar.-Apr. 2008.

* cited by examiner

CURRENT CONTROL FOR ELECTROTRANSPORT DRUG DELIVERY

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to an electrotransport drug delivery device. In particular, the invention is directed to a constant current supply circuit which has improved safety.

BACKGROUND

A variety of drug delivery systems, including automatic drug delivery systems, are known. Because the consequences of delivering an inappropriate dosage (e.g., too much or too little) of a drug can be life threatening, it is of critical importance that drug delivery systems be extremely accurate. Drug delivery systems that are configured to deliver medication to patients must be configured to prevent even unlikely accidental delivery events. In particular, drug delivery systems that electrically delivery drug to a patient, including transdermal or other electrotransport drug delivery devices, be prevented from accidentally providing drug to the patient.

The term "electrotransport" as used herein refers generally to the delivery of an agent (e.g., a drug) through a membrane, such as skin, mucous membrane, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid. The liquid contains the agent to be delivered, under the influence of an electric field. Still another type of electrotransport process, electroporation, involves the formation of transiently-existing pores in a biological membrane by the application of an electric field. An agent can be delivered through the pores either passively (i.e., without electrical assistance) or actively (i.e., under the influence of an electric potential). However, in any given electrotransport process, more than one of these processes may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, regardless of the specific mechanism or mechanisms by which the agent actually is transported.

In general, electrotransport devices use at least two electrodes that are in electrical contact with some portion of the skin, nails, mucous membrane, or other surface of the body. One electrode, commonly called the "donor" or "active" electrode, is the electrode from which the agent is delivered into the body. The other electrode, typically termed the "counter" or "return" electrode, serves to close the electrical circuit through the body. For example, if the agent to be delivered is positively charged, i.e., a cation, then the anode is the active or donor electrode, while the cathode serves to complete the circuit. Alternatively, if an agent is negatively charged, i.e., an anion, the cathode is the donor electrode. Additionally, both the anode and cathode may be considered donor electrodes if both anionic and cationic agent ions, or if uncharged dissolved agents, are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically, one pole of the power source is electrically connected to the donor electrode, while the opposite pole is electrically connected to the counter electrode. In addition, some electrotransport devices have an electrical controller that controls the current applied through the electrodes, thereby regulating the rate of agent delivery. Furthermore, passive flux control membranes, adhesives for maintaining device contact with a body surface, insulating members, and impermeable backing members are some other potential components of an electrotransport device.

Small, self-contained electrotransport drug delivery devices adapted to be worn on the skin for extended periods of time have been proposed. See, e.g., U.S. Pat. Nos. 6,171,294, 6,881,208, 5,843,014, 6,181,963, 7,027,859, 6,975,902, and 6,216,033. These electrotransport agent delivery devices typically utilize an electrical circuit to electrically connect the power source (e.g., a battery) and the electrodes. The electrical components in such miniaturized iontophoretic drug delivery devices are also preferably miniaturized, and may be in the form of either integrated circuits (i.e., microchips) or small printed circuits. Electronic components, such as batteries, resistors, pulse generators, capacitors, etc. are electrically connected to form an electronic circuit that controls the amplitude, polarity, timing waveform shape, etc. of the electric current supplied by the power source. Other examples of small, self-contained electrotransport delivery devices are disclosed in U.S. Pat. Nos. 5,224,927; 5,203,768; 5,224,928; and 5,246,418.

Figure 1:
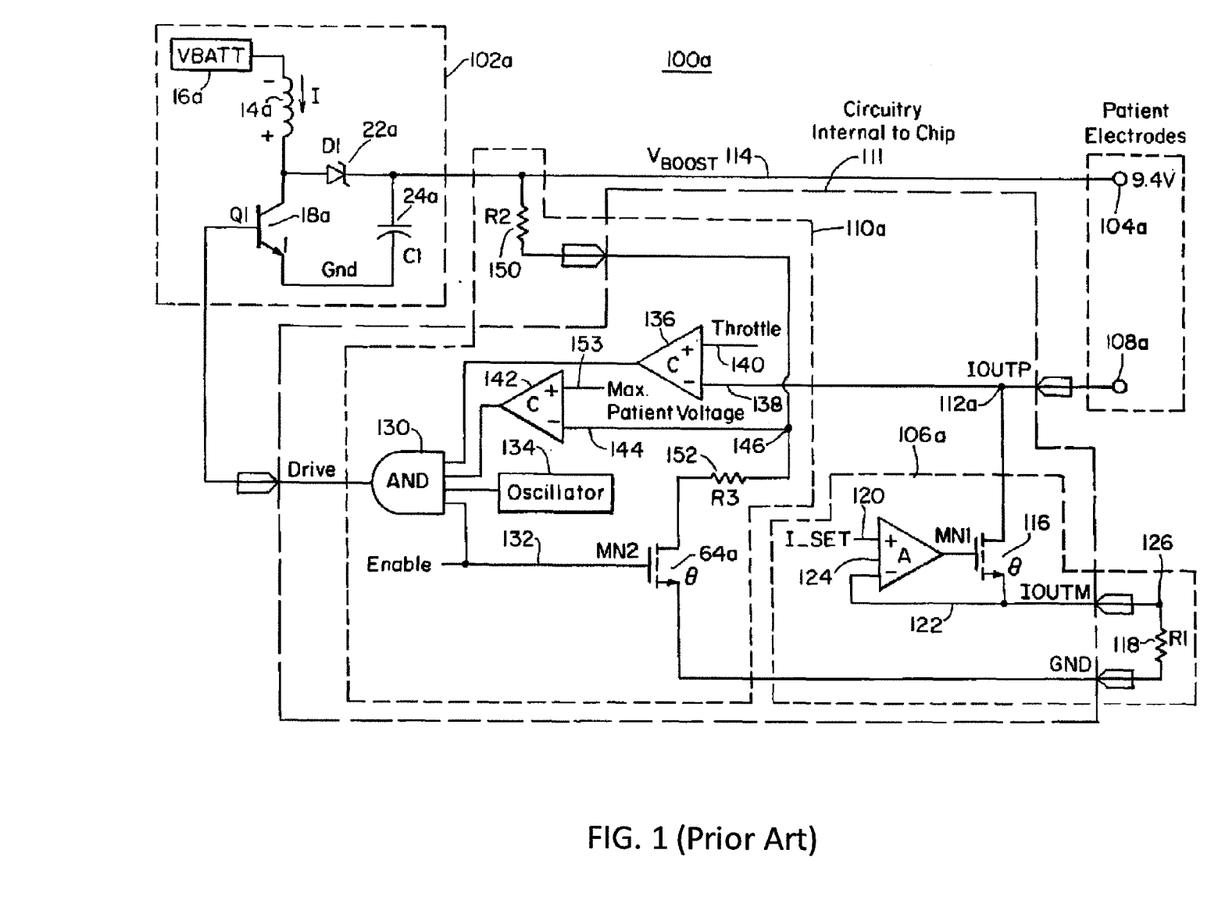
FIG. 1 is a schematic of a prior art iontophoretic transdermal drug delivery system.

Constant current supplies for variable resistance loads such as those appropriate for use with an electrotransport drug delivery device have been previously described, however such systems require the use of the cathode to determine the voltage and/or current at the cathode. For example, U.S. Pat. No. 5,804,957 to Coln describes a constant current supply system for a variable resistance load. This system includes a constant current circuit connected to a second output terminal (e.g., anode) for providing a predetermined current to the load (patient) and a constant control circuit. A voltage supply control circuit monitors the voltage at the second terminal across the constant current circuit and adjusts the voltage supply to maintain the second terminal at a preselected voltage for maintaining the predetermined current to the variable resistance load. See, e.g., FIG. 1, which illustrates a prior art system including a voltage control circuit that directly monitors the cathode (via a comparator "throttle" element 140).

However in some variations it may be beneficial to control and monitor the applied current without directly monitoring the second patient terminal (e.g., cathode). This configuration allows separation of the control aspect of the circuit from the risk management aspect of the circuitry.

For example, described herein are methods, devices and systems for monitoring and controlling electrotransport drug delivery devices including indirectly monitoring and controlling the circuit not directly connected to the patient terminal (e.g., cathode) using a switching element.

SUMMARY OF THE DISCLOSURE

In general, described herein are devices and methods for controlling the application of current and/or voltage to deliver drug from patient contacts of an electrotransport drug delivery device by indirectly controlling and/or monitoring the applied current without directly measuring from the cathode of the patient terminal. In particular, described herein are electrotransport drug delivery systems including constant current delivery systems having a feedback current and/or voltage control module that is isolated from the patient contacts (e.g., anodes and cathodes). In some variations the feedback module is isolated by a transistor from the patient contacts; feedback current and/or voltage control measurements are performed at the transistor rather than at the patient contact (e.g., cathode).

For example, described herein are electrotransport drug delivery systems having a constant current supply. In some variations the system include: a power source; a first patient contact connected to a power source; a second patient contact connected to a current control transistor; and a sensing circuit for measuring voltage at the transistor, wherein the second patient contact is connected to the sensing circuit only through the current control transistor so that the second patient contact is electrically isolated from the sensing circuit. In some variations, the first patient contact may also be connected indirectly to the power source.

The current control transistor may be controlled by an amplifier receiving input from a microcontroller. Any appropriate transistor may be used. For example, the transistor may be a FET or a bipolar transistor. In variations in which the current control transistor is a FET, the second patient contact may be connected to the drain of the transistor.

In some variations, the sensing circuit is configured to compare the voltage at the transistor to a threshold voltage. The sensing circuit may provide input to a feedback circuit. In some variations, this feedback circuit may provide an alarm based on the comparison between the voltage at the transistor (e.g., at the gate of the transistor when the drain is patient-contacting) and the threshold voltage to indicate constant current cannot be maintained. The feedback circuit may automatically control the power source based on the comparison between the voltage at the transistor and the threshold voltage to maintain constant current while minimizing power consumption. For example, in some variations, the current may be maintained at about 170 µA.

Also described herein are electrotransport drug delivery systems having a constant current supply, the system comprising: a power source; a first patient contact connected to the power source; a second patient contact connected to a transistor (e.g., a drain of a transistor); a current control feedback circuit for providing a control signal to the transistor when the connection between the first patient contact and the second patient contact is closed; wherein the transistor is connected to the second patient contact; and a sensing circuit for measuring a voltage applied at the transistor when the connection is closed; wherein the second patient contact is connected to the current control feedback circuit and sensing circuit only though the transistor. For example, the second patient contact may be connected to the drain of the transistor, which is separate from the feedback/sensing circuit that may be connected to the gate of the transistor.

As mentioned above, the transistor may be any appropriate transistor, including a bipolar transistor and/or a field-effect transistor (FET). For example, if the transistor is a FET, the second patient contact may be connected to a drain of the transistor, and the control signal may comprise a voltage applied to a gate of the transistor. In some variations the transistor is a bipolar transistor, and the second patient contact is connected to a collector, while the control signal comprises a current applied to the base of the bipolar transistor. In general, the control signal may be a voltage and/or a current applied to the transistor.

In some variations, the control signal provided to the transistor may be controlled by an amplifier receiving input from a microcontroller.

The feedback circuit may control the voltage applied to the power source. For example, in some variations, the feedback circuit compares the transistor (e.g., gate) voltage to a reference voltage. The feedback circuit controls the power source based on the comparison between the transistor gate voltage and the reference voltage. The feedback circuit may provide a power source sufficient to deliver a constant current. For example, the feedback circuit may provide a power source sufficient to deliver a constant current of about 170 µA. The feedback circuit may include a digital to analogue converter for providing a constant current.

In general, the sensing circuit may be isolated (e.g., electrically isolated) from the first and second patient contacts by the transistor. The transistor may be located between the second patient contact and a sense resistor.

The first patient contact may be an anode and the second patient contact may be a cathode. The connection between the first patient contact and the second patient contact is typically configured to be closed (e.g., connected) by a patient's skin.

Also described herein are methods for operating an electrotransport drug delivery system including a constant current supply, the method comprising: contacting a patient's skin with an anode and cathode to form a connection between the anode and cathode; applying an anode voltage to the anode; providing a control signal to a transistor (e.g., gate) connected to the cathode (e.g., at the drain); detecting a voltage at the transistor, wherein the cathode is isolated from the voltage detection by the transistor; comparing the transistor voltage to a threshold voltage; and controlling the anode voltage applied to the anode based on the comparison between the transistor voltage and the threshold voltage.

The methods may include the use of any appropriate transistor. For example, the transistor may be a FET and the control signal comprises a voltage applied to a gate of the transistor. The anode voltage may be applied to the anode in response to an input. The control signal applied to the transistor may be provided to the transistor by an amplifier, the amplifier isolated from the anode and the cathode by the transistor. As mentioned above, any appropriate control signal may be used, in particular an electrical voltage and/or a current.

In any of these variations, the current provided from the transistor is a constant current. For example, the provided current may be controlled to be about 170 µA.

In some variations, the method includes adjusting the voltage applied to the anode based on the comparison of the transistor voltage to the threshold voltage.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Reference will now be made in detail to exemplary embodiments of the invention, examples of which are illustrated in the accompanying drawings. While the invention will be described in conjunction with the exemplary embodiments, it will be understood that they are not intended to limit the invention to those embodiments. On the contrary, the invention is intended to cover alternatives, modifications and equivalents, which may be included within the spirit and scope of the invention as defined by the appended claims.

One method for transdermal delivery of active agents involves the use of electrical current to actively transport the active agent into the body through intact skin by electrotransport. Electrotransport techniques may include iontophoresis, electroosmosis, and electroporation. Electrotransport devices, such as iontophoretic devices are known in the art. One electrode, which may be referred to as the active or donor electrode, is the electrode from which the active agent is delivered into the body. The other electrode, which may be referred to as the counter or return electrode, serves to close the electrical circuit through the body. In conjunction with the patient's body tissue, e.g., skin, the circuit is completed by connection of the electrodes to a source of electrical energy, and usually to circuitry capable of controlling the current passing through the device when the device is "on" delivering current. If the substance to be driven into the body is ionic and is positively charged, then the positive electrode (the anode) will be the active electrode and the negative electrode (the cathode) will serve as the counter electrode. If the ionic substance to be delivered is negatively charged, then the cathodic electrode will be the active electrode and the anodic electrode will be the counter electrode.

A switch-operated therapeutic agent delivery device can provide single or multiple doses of a therapeutic agent to a patient by activating a switch. Upon activation, such a device delivers a therapeutic agent to a patient. A patient-controlled device offers the patient the ability to self-administer a therapeutic agent as the need arises. For example, the therapeutic agent can be an analgesic agent that a patient can administer whenever sufficient pain is felt.

As described in greater detail below, any appropriate drug (or drugs) may be delivered by the devices described herein. For example, the drug may be an analgesic such as fentanyl (e.g., fentanyl HCL) or sufentanil.

In some variations, the different parts of the electrotransport system are stored separately and connected together for use. For example, examples of electrotransport devices having parts being connected together before use include those described in U.S. Pat. No. 5,320,597 (Sage, Jr. et al); U.S. Pat. No. 4,731,926 (Sibalis), U.S. Pat. No. 5,358,483 (Sibalis), U.S. Pat. No. 5,135,479 (Sibalis et al.), UK Patent Publication GB2239803 (Devane et al), U.S. Pat. No. 5,919,155 (Lattin et al.), U.S. Pat. No. 5,445,609 (Lattin et al.), U.S. Pat. No. 5,603,693 (Frenkel et al.), WO1996036394 (Lattin et al.), and US 2008/0234628 A1 (Dent et al.).

In general, the systems and devices described herein include an anode and cathode for the electrotransport of a drug or drugs into the patient (e.g., through the skin or other membrane) and a controller for controlling the delivery (e.g., turning the delivery on or off); all of the variations described herein may also include an off-current module for monitoring the anode and cathode when the device is off (but still powered) to determine if there is a potential and/or current (above a threshold value) between the anode and cathode when the controller for device has otherwise turned the device "off" so that it should not be delivering drug to the patient. The controller may include an activation controller (e.g., an activation module or activation circuitry) for regulating the when the device is on, applying current/voltage between the anode and cathode and thereby delivering drug.

Throughout this specification, unless otherwise indicated, singular forms "a", "an" and "the" are intended to include plural referents. Thus, for example, reference to "a polymer" includes a single polymer as well as a mixture of two or more different polymers, "a contact" may refer to plural contacts, "a post" may indicate plural posts, etc.

As used herein, the term "user" indicates anyone who uses the device, whether a healthcare professional, a patient, or other individual, with the aim of delivering a therapeutic agent to a patient.

Figure 2:
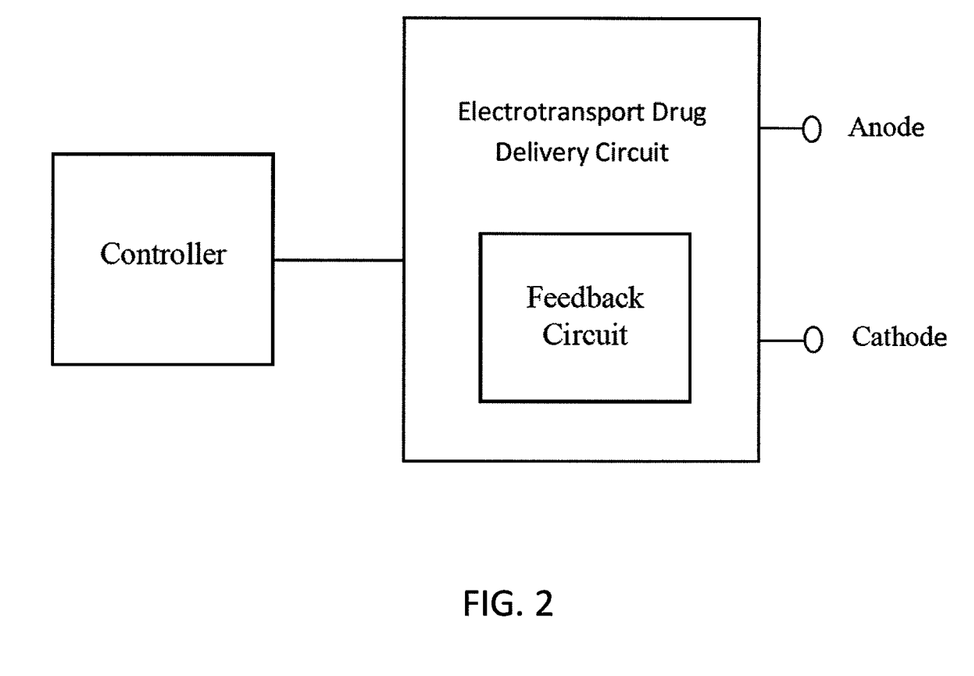
FIG. 2 is a block diagram of an exemplary electrotransport drug delivery circuit for use with an electrotransport drug delivery system including a controller, a drug delivery circuit, a feedback circuit, an anode and a cathode.

In general, the devices described herein may include control logic and/or circuitry for regulating the application of current by the device. For example, FIG. 2 illustrates a schematic for controlling the application of current to deliver drug. A feedback circuit may be controlled or regulated by a controller and be part of (or separate from) the drug delivery circuit. The controller and circuit may include hardware, software, firmware, or some combination thereof (including control logic). For example, as illustrated in FIG. 2, a system may include an anode, cathode and feedback circuit. The feedback circuit may form part (or be used by) the drug delivery module to provide current between the anode and cathode and deliver drug. The device may also include a controller controlling operation of the device. The controller may include a processor or ASIC.

Figure 3:
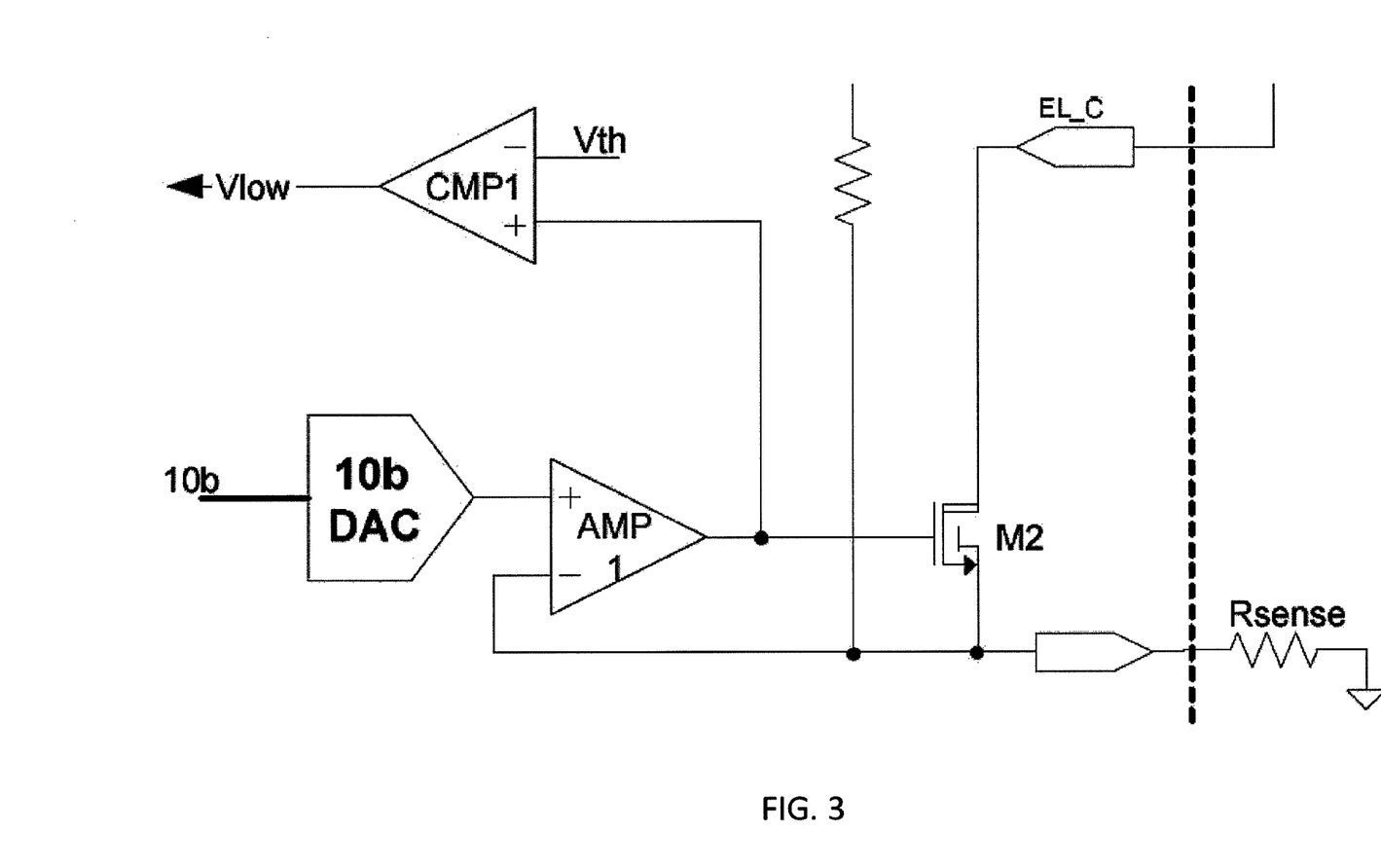
FIG. 3 is a schematic diagram of the feedback circuit of FIG. 2.

In general, the feedback circuit may be referred to as a type of self-test that is performed by the device. FIG. 3 illustrates one variation of a feedback circuit for controlling the current and/or voltage applied across the patient electrodes (anode and cathode), and is included and described in greater detail below in the context of FIG. 4.

Figure 4:
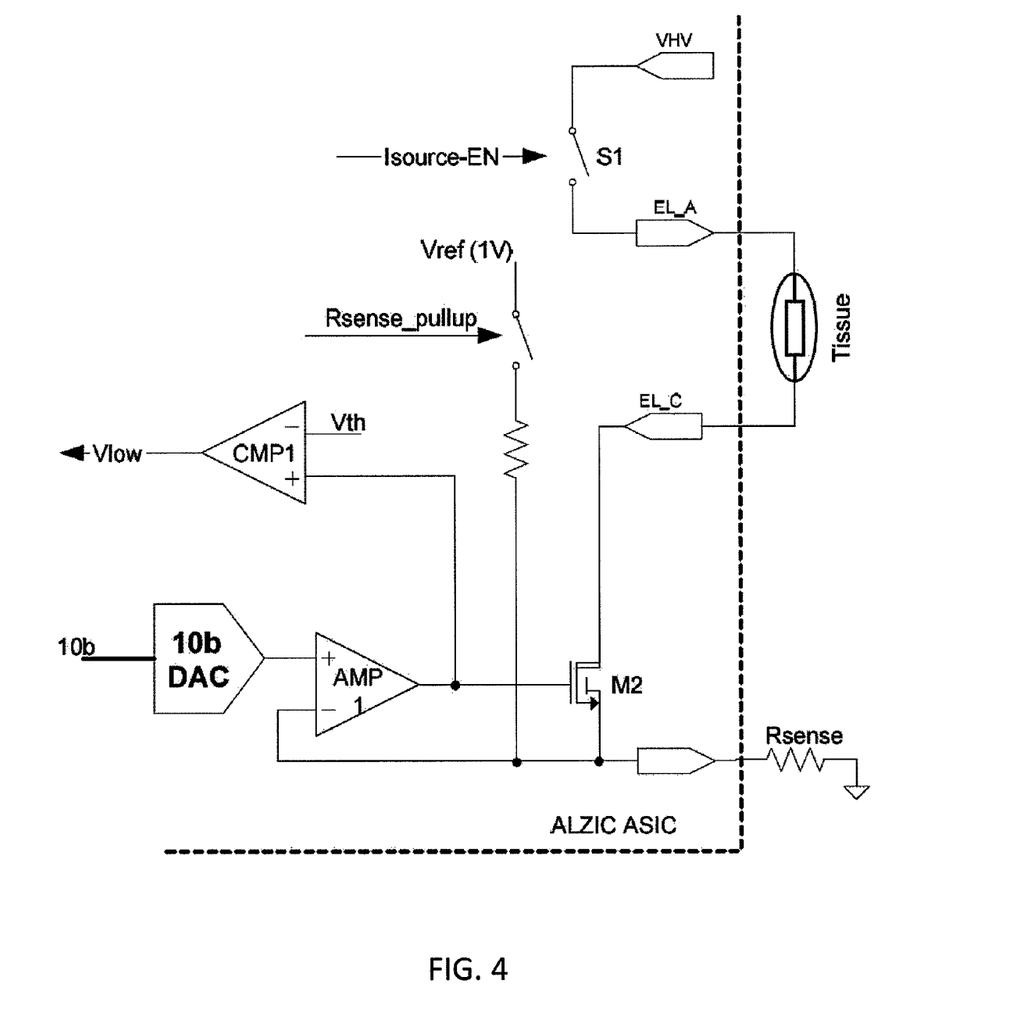
FIG. 4 is a schematic diagram of the electrotransport drug delivery circuit of FIG. 2.

FIG. 4 illustrates one variation of a diagram illustrating the circuit controlling the application of current to deliver drug to a patient. In this example, the drug dose is regulated by the control of the current through the electrodes (anode to cathode). The current in this example is programmable (e.g., using a 10 bit DAC), but may be preset. For example, the target current may be preset to deliver a dose using a current of 170 µA, as illustrated.

In FIG. 4, the dotted line schematically indicates ASIC components; this integrated circuit may be separate from the Rsense resistor. The patient tissue ("tissue") completes the circuit between the anode and cathode elements. In some variations Rsense is on the printed circuit board. The Rsense may be on the circuit board (e.g., but not within the ASICS). For example, the Rsense and everything within the dotted box may be on the printed circuit board. The anode and the cathode may be connected to the patient.

In FIG. 4, above the anode is a VHV, which is the voltage source that applies the voltage to deliver a current and therefore drive delivery of drug. In some variations a Vboost may also be included as part of (or in connection with) the VHV. In addition, a switch, S1, may be included as a software-enabled switch to control the application of voltage to the anode. The S1 switch may act as a safety feature to control (via software) when current is not delivered. The voltage may be turned off completely and the switch opened so that even if there were some other voltage present, the anode would be floating. Thus, current could not be pulled through the anode to cathode because the anode is floating (and there is no source of electrons to pull current through, since it is a completely open circuit).

In this example, when the S1 switch is closed, current may then flow from the anode, through the tissue, and return through the cathode to the M2 switch (transistor). In this example, the M2 switch is a transistor (e.g., a field effect transistor) that acts as a valve to control the flow of current. The M2 switch may be referred to as a current control valve or throttle that regulates the current flow down to Rsense resistor, where it goes to the ground. Schematically, the current is throttled by the M2 switch, which may allow control of the current at various levels. For example, in FIG. 4, the current level is set to be approximately 170 uA. In this example, Rsense may be used to set the current range, and/or the maximum value. A square wave of current may be delivered.

Further, M2 may be regulated by an amplifier (e.g., Amp1). In this example, Amp1 is an analogue amplifier; the input to Amp1 is a digital to analogue converter (DAC), which is set with the target 170 µA level. Thus, a microcontroller may be used to set a digital signal using an analogue to digital converter, corresponding to the target delivery current (e.g., 170 µA).

Thus, in operation, the controller (e.g., microcontroller) may be configured so that when no current is to be delivered the DAC may be set to 0 and when current is to be delivered, it may be set to 170 uA, providing an analogue output to AMP1 that allows current to flow to Rsense. Thus, the input to M2 (gate) may be used to monitor the voltage at the transistor gate using a comparator, e.g., CMP1. In some variations the voltage at the gate is compared to a threshold (Vthreshold). If the voltage at the gate of M2 is low, it may be increased, and if it is high, it may be decreased. This feedback may be used to adjust VHV, as illustrated in FIG. 4.

Because the cathode is connected only to the current control transistor and not directly connected to the sensing circuit, potential faults in the sensing circuit are isolated from the second patient contact and could not result in additional current flow from anode to cathode, and therefore could not result in additional drug delivered to the patient.

The voltage may be changed to set the current with that DAC and AMP1. For example, the current may be set to 170 uA, and the control system described herein prevents it from going over 170 uA, providing a constant current source. That DAC, AMP1 and M2 limit the maximum amount of current that can flow through M2. Setting the DAC to 170 uA prevents the current from exceeding 170 uA regardless of the voltage. In this configuration, if the voltage is higher than it has to be, then by Ohms law, V=IR, where R is the skin resistance and I is the target 170 uA, the voltage can be limited. The M2 throttles the maximum amount of current to limit it to 170 uA, allowing the voltage to be adjusted. Since the power equals the current times the voltage, when the current is fixed (e.g., to 170 µA) the amount of power can be minimized by providing only the minimum amount of voltage. This may help conserve the batter power by using just use the minimum amount of voltage required. In practice the control and monitoring circuit may do this by adjusting the voltage to automatically drop the voltage as necessary. Monitoring the gate at M2 to maintain saturation so that the source voltage VHV value is kept above the level sufficient to deliver current at the set (e.g., 170 µA) value. Below the saturation level, the gate may deliver less than 170 uA. To prevent this, the voltage is allowed to drop until it reaches a limit at which it is saturated; and as soon as this threshold is reached, the comparator may sense that the saturation and may adjust the voltage back up. This feedback (voltage feedback) takes place at the level of the M2 gate (throttle) and provides a constant feedback loop where it is constantly comparing the gate of the M2 to a threshold value.

Because this feedback loop occurs at the throttle, e.g., rather than the cathode (by, for example, monitoring the voltage at the cathode), additional benefits may be realized. Monitoring the voltage at that gate (M2) to control the VHV allows control of the boost voltage without altering (e.g., touching) the cathode at all, e.g., maintaining the monitoring and control aspects of the system in electrical isolation. This allows separation of the control aspect from a risk management aspect of the device, preventing the device from applying inappropriate current and thereby drug. In operation, self-checks measuring the anode-cathode voltage may be performed independently of the control of the voltage and/or current across the anode and cathode, since the cathode (and/or anode) is not used for monitoring. Instead, the cathode is used to deliver the drug.

This configuration allows control of the voltage to reduce power consumption, and/or monitoring and controlling the voltage without having to monitor at the cathode, resulting in an efficiency of the system by monitoring at the throttle point where the system can meet safety objectives while only making measurements at the anode and cathode that are related to current flow through the anode cathode. Thus, the cathode does not require connection of a measurement line to the electrode (e.g., cathode). Control of the voltage is therefore independent of safety features such as error detection (e.g., leak current detection). Further, this architecture separates the voltage control mechanism from such an error detection mechanism. Error detection mechanisms may include (e.g., within the ASICS) an analogue to digital convertor and the analogue to digital convertor multiplexed to measure the voltage at the anode, the cathode, the VHV voltage, or the like. However, the feedback detection and control of the voltage and current may be regulated from the cathode (e.g., gate M2) rather than the level of the cathode.

The advantage of this logical separation may include making only measurements on that anode and cathode that are related to whether or not there is leakage current present (whether or not there is a safety problem). Measurements at the gate M2 may be constantly ongoing (e.g., every couple of clock ticks); it is not necessary to measure at the cathode in this configuration, so that the cathode remains isolated from the feedback circuit through the gate M2. The anode cathode measurement is independent verification that there is no current flowing there. By configuring the system in this manner, the cathode is isolated from the feedback that is controlling the voltage. Separation permits the feedback mechanism to be separate from the actual patient connection delivering the current. Thus, the voltage is less critical for patient safety and the monitoring and controlling of the voltage is configured to provide efficiency of the system and the battery power. Current may flow through the drain to the source of the transistor without requiring additional circuitry between the cathode and ground, reducing the chance for malfunction (e.g., additional current flow) through this additional current path. Patient safety can be dramatically affected by even small errors in the circuitry. Thus, in some variations, the system is limited so that the only connections to the anode/cathode are those that must be there, as shown and described herein.

In some variations, the systems and methods described herein use a gate (e.g., transistor M2) to isolate the patient connections, e.g., anode and cathode, from the feedback module used to control the applied voltage and to regulate the current between the patient connections. In this example, the feedback module is configured as a circuit including a comparator that compares the voltage on the transistor to a threshold voltage.

In some variations this circuit regulates the current between the patient connections so that it rides at or below the target current level (e.g., 170 μA). The circuit may sense when the current is above 170 uA.

Figure 5:
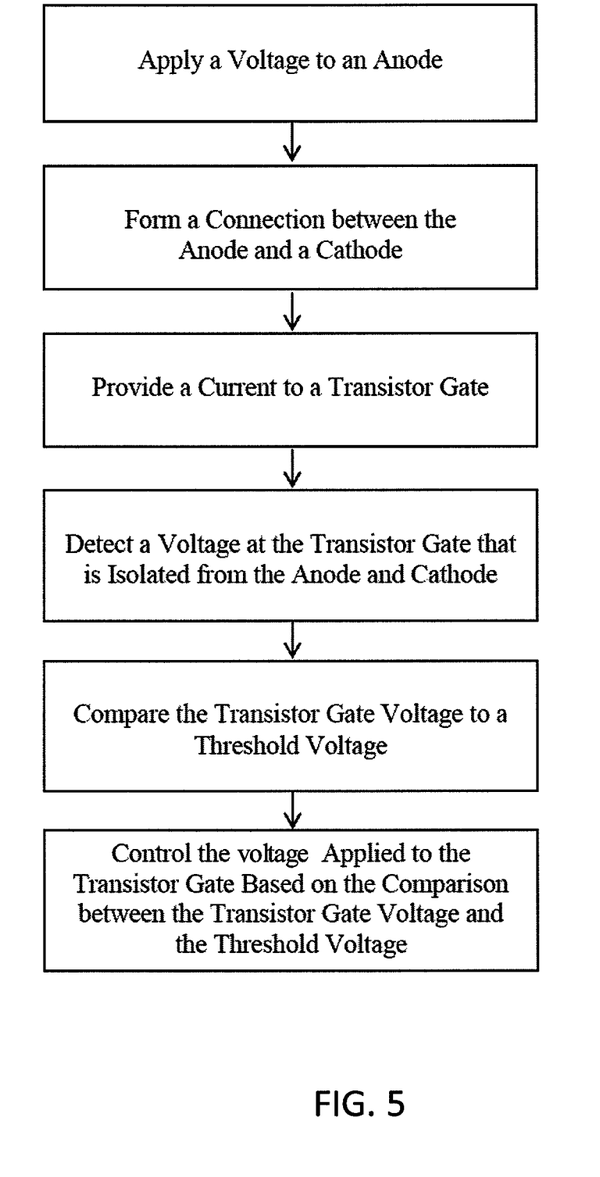
FIG. 5 is a flow diagram of a method of operation of an exemplary electrotransport drug delivery circuit.

FIG. 5 schematically illustrates one variation of a method for regulating the voltage and/or current across the patient connections (e.g., anode and cathode) of an electrotransport drug delivery system. In this example, a pair of patient connections are configured to contact a patient tissue (e.g., skin) to complete the patient circuit. The first patient connection (in some configurations the anode, in other configurations, the cathode) is connected to a driving voltage source. The connection between the driving voltage source and the first patient connection may be regulated by a switch or gate, which may be regulated or controlled (e.g., by a microcontroller). The second patient connection (e.g., in some variations a cathode, in other variations an anode) is then connected in series to a transistor drain (or other throttle element), and a feedback module for monitoring and controlling the current and voltage applied between the first and second patient connections are isolated from the second patient connection by this transistor gate.

In operation, a voltage is first applied to the first patient connection (e.g., anode) after or before a connection is made by skin contact between the first and second patient connections. Current is then provided to the transistor drain downstream of the second patient contact, and a feedback module determines the voltage at the transistor gate in isolation of the first and second patient contacts. The voltage at the transistor gate is compared to a threshold voltage and this comparison is used to adjust the applied voltage at the first patient connection. In the same example, a target current may be provided (e.g., from a microcontroller) to the transistor to regulate the current between the first and second patient connections.

The constant current supply described above may be used to regulate the dosing of the system to deliver a target current (e.g., drug delivery current) at a low voltage even with variable patient resistances. For example, the circuit shown in FIGS. 3 and 4 may be used to provide a dose of drug by delivering a predetermined 170 μA drug delivery current over a dosing period (e.g., a 10 minute dose). The circuit controlling the anode and cathode shown in FIGS. 3 and 4 includes a control block containing circuitry to connect the output of the voltage boost converter (VHV) to the anode electrode (EL_A) through the switch S1. A 10 bit DAC is used to configure the current output to a set value proportional to the desired dosing current. The DAC drives AMP1 which controls the current flowing through EL_A and EL_C by driving the gate of M2. The source of M2 determines the current flow through Rsense which causes the voltage drop that is fed back into AMP1. As the skin resistance between EL_A and EL_C varies, so does the current through Rsense, which triggers a change in the output of AMP1. AMP1 becomes saturated if there is not sufficient voltage to deliver the programmed current with the resistance between EL_A and EL_C. Driver functions are available to control and monitor various the points of this circuit.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. An electrotransport drug delivery system having a power source that is controlled by feedback circuitry that is isolated from a patient terminal, the system comprising:
   the power source;
   the patient terminal comprising a first patient contact connected to the power source and a second patient contact connected to an isolation circuit; and
   a sensing circuit configured to measure voltage, current or voltage and current at the isolation circuit, wherein the sensing circuit is configured to provide feedback controlling power at the first patient contact, wherein the second patient contact is connected to the sensing circuit only through the isolation circuit so that the second patient contact is electrically isolated from the sensing circuit.

2. The system of claim 1, wherein the isolation circuit comprises a transistor.

3. The system of claim 1, wherein the isolation circuit comprises a current control transistor controlled by an amplifier receiving input from a microcontroller.

4. The system of claim 1, wherein the sensing circuit is configured to compare the voltage, current or current and voltage at the isolation circuit to a threshold.

5. The system of claim 4 wherein the feedback circuit automatically controls the power source based on the comparison between the voltage, current or voltage and current at the isolation circuit and the threshold to regulate an applied current.

6. The system of claim 4 wherein the feedback circuit automatically controls the power source based on the comparison between the voltage, current or voltage and current at the isolation circuit and the threshold to regulate an applied current while minimizing power consumption.

7. The system of claim 1, wherein the sensing circuit provides input to a feedback circuit.

8. An electrotransport drug delivery system having a power source that is controlled by feedback circuitry that is isolated from a patient terminal, the system comprising:
   the power source;
   the patient terminal comprising a first patient contact connected to the power source and a second patient contact connected to an isolation circuit;
   a feedback circuit configured to provide a control signal to the isolation circuit when the connection between the first patient contact and the second patient contact is closed; and
   a sensing circuit configured to measure voltage, current or current and voltage at the isolation circuit when the connection is closed, wherein the sensing circuit is configured to provide feedback controlling power at the first patient contact;
   wherein the second patient contact is connected to the feedback circuit and sensing circuit only though the isolation circuit.

9. The system of claim 8, wherein the isolation circuit comprises a transistor, and further wherein the second patient contact connected to a drain of the transistor and the control signal comprises a voltage applied to a gate of the transistor.

10. The system of claim 8, wherein the control signal provided to the isolation circuit is controlled by an amplifier receiving input from a microcontroller.

11. The system of claim 8, wherein the feedback circuit controls a voltage applied to the power source.

12. The system of claim 8, wherein the feedback circuit compares the voltage, current or current and voltage measured at the isolation circuit to a reference voltage or current.

13. The system of claim 12, wherein the feedback circuit controls the power source based on the comparison between the voltage measured at the isolation circuit and the reference voltage.

14. The system of claim 8, wherein the sensing circuit is isolated from the first and second patient contacts by the isolation circuit.

15. The system of claim 8, wherein the first patient contact is an anode and the second patient contact is a cathode.

16. The system of claim 8, wherein the power source is configured to deliver a constant current.

17. The system of claim 8, wherein the power source and feedback circuit are configured to deliver a constant current of about 170 µA.

18. The system of claim 8, wherein the connection between the first patient contact and the second patient contact is configured to be closed by a patient's skin.

19. The circuit of claim 8, wherein the isolation circuit comprises a transistor located between the second patient contact and a sense resistor.

20. The system of claim 8, wherein the feedback circuit includes a digital to analogue converter for providing a constant current.

* * * * *